US010702719B2

(12) United States Patent
Khokhlova et al.

(10) Patent No.: US 10,702,719 B2
(45) Date of Patent: Jul. 7, 2020

(54) HISTOTRIPSY TREATMENT OF HEMATOMA

(71) Applicant: University of Washington, Seattle, WA (US)

(72) Inventors: Tatiana Khokhlova, Seattle, WA (US); Thomas J. Matula, Seattle, WA (US); Wayne L. Monsky, Seattle, WA (US); Yak-Nam Wang, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 633 days.

(21) Appl. No.: 15/288,372

(22) Filed: Oct. 7, 2016

(65) Prior Publication Data

US 2017/0100145 A1 Apr. 13, 2017

Related U.S. Application Data

(60) Provisional application No. 62/239,751, filed on Oct. 9, 2015.

(51) Int. Cl.
*A61N 7/02* (2006.01)
*A61B 17/22* (2006.01)

(52) U.S. Cl.
CPC ...... *A61N 7/02* (2013.01); *A61B 2017/22008* (2013.01); *A61B 2017/22079* (2013.01); *A61B 2217/005* (2013.01)

(58) Field of Classification Search
CPC .............. A61N 7/02; A61N 2007/0039; A61N 2007/0052; A61B 2217/005; A61B 2017/22008; A61B 2017/22079; A61B 8/085
See application file for complete search history.

(56) References Cited

U.S. PATENT DOCUMENTS

| 6,432,053 | B1* | 8/2002 | Fecht | A61B 5/1075 |
| | | | | 600/437 |
| 2011/0054363 | A1* | 3/2011 | Cain | A61B 17/225 |
| | | | | 601/4 |
| 2012/0065494 | A1* | 3/2012 | Gertner | A61B 5/055 |
| | | | | 600/411 |
| 2012/0259250 | A1* | 10/2012 | Sapozhnikov | A61N 7/02 |
| | | | | 601/2 |

OTHER PUBLICATIONS

Park et al., "Non-Invasive Embolus Trap Using Histotripsy—An Acoustic Parameter Study", Ultrasound in Med. & Biol., vol. 39, No. 4, pp. 611-619, 2013 (Year: 2013).*

(Continued)

*Primary Examiner* — Angela M Hoffa
*Assistant Examiner* — Aminah Asghar
(74) *Attorney, Agent, or Firm* — Kilpatrick Townsend & Stockton LLP

(57) ABSTRACT

Methods for treating an extravascular hematoma in a patient can include liquefying a first portion of the extravascular hematoma by applying a first series of focused acoustic pulses to the extravascular hematoma at a first frequency; and liquefying a second portion of the extravascular hematoma by applying a second series of focused acoustic pulses to the extravascular hematoma at a second frequency. Liquefied remains of the extravascular hematoma can be aspirated from the patient following liquefaction and disruption.

17 Claims, 17 Drawing Sheets

(56) References Cited

OTHER PUBLICATIONS

Bader et al., "Shaken and Stirred: Mechanisms of Ultrasound-Enhanced Thrombolysis", Ultrasound in Med. & Biol., vol. 41, No. 1, 2015, pp. 187-196.
Canney et al., "Shock-Induced Heating and Millisecond Boiling in Gels and Tissue Due to High Intensity Focused Ultrasound", Ultrasound in Med. & Biol., vol. 36, No. 2,, 2010, pp. 250-267.
Conforti, "The Treatment of Muscle Hematomas", Chapter from the book Muscle Injuries in Sport Medicine, 2013, pp. 202-220.
Garner et al., "Compartment Syndrome: Diagnosis, Management, and Unique Concerns in the Twenty-First Century", HSS Journal, The Musculoskeletal Journal of Hospital for Special Surgery, vol. 10, 2014, pp. 143-152.
Khokhlova et al., "Controlled tissue emulsification produced by high intensity focused ultrasound shock waves and millisecond boiling", J. Acoust. Soc. Am. vol. 130 (5), Nov. 2011, pp. 3498-3510.
Khokhlova et al., "Histotripsy Methods in Mechanical Disintegration of Tissue: Toward Clinical Applications", Int J Hyperthermia, vol. 31(2), Mar. 2015, pp. 145-162.
Khokhlova et al., "Ultrasound-guided tissue fractionation by high intensity focused ultrasound in an in vivo porcine liver model", PNAS, vol. 111, No. 22, Jun. 3, 2014, pp. 8161-8166.
Kim et al., "Rapid Prototyping Fabrication of Focused Ultrasound Transducers", IEEE Transactions on Ultrasonics, Ferroelectrics, and Frequency Control, vol. 61, No. 9, Sep. 2014, pp. 1559-1574.
Maxwell et al., "Cavitation clouds created by shock scattering from bubbles during histotripsy", J. Acoust. Soc. Am. vol. 130 (4), 2011, pp. 1888-1898.
Maxwell et al., "Histotripsy methods in mechanical disintegration of tissue: Towards clinical applications", Int J Hyperthermia, vol. 31(2), 2015, pp. 145-162.
Maxwell et al., "Non-Invasive Thrombolysis Using Pulsed Ultrasound Cavitation Therapy—Histotripsy", Ultrasound Med Biol., vol. 35(12), 2009, pp. 1982-1994.
Maxwell et al., "Noninvasive treatment of deep venous thrombosis using pulsed ultrasound cavitation therapy (histotripsy) in a porcine model", J Vasc Interv Radiol. vol. 22(3), 2011, pp. 369-377.
Nahirnyak et al., "Acousto-mechanical and thermal properties of clotted blood a)", J Acoust Soc Am., vol. 119(6), 2006, pp. 3766-3772.
Park et al., "Non-Invasive Embolus Trap (NET) using Histotripsy—An Acoustic Parameter Study", Ultrasound Med Biol. vol. 39(4), 2013, pp. 611-619.
Parsons et al., "Pulsed Cavitational Ultrasound Therapy for Controlled Tissue Homogenization", Ultrasound in Med. & Biol., vol. 32, No. 1, 2006, pp. 115-129.
Simon et al., "Ultrasonic atomization of tissue and its role in tissue fractionation by high intensity focused ultrasound", Phys. Med. Biol. vol. 57, 2012, pp. 8061-8078.
Smith et al., "The physiotherapy management of muscle haematomas", Physical Therapy in Sport, vol. 7, 2006, pp. 201-209.
Wang et al., "Histological and Biochemical Analysis of Mechanical and Thermal Bioeffects in Boiling Histotripsy Lesions Induced by High Intensity Focused Ultrasound", Ultrasound Med Biol. vol. 39(3), 2013, pp. 424-438.
Wicks et al., "Gray Scale Features of Hematomas: An Ultrasonic Spectrum", Am J Roentgenol, vol. 131, Dec. 1978, pp. 977-980.

\* cited by examiner

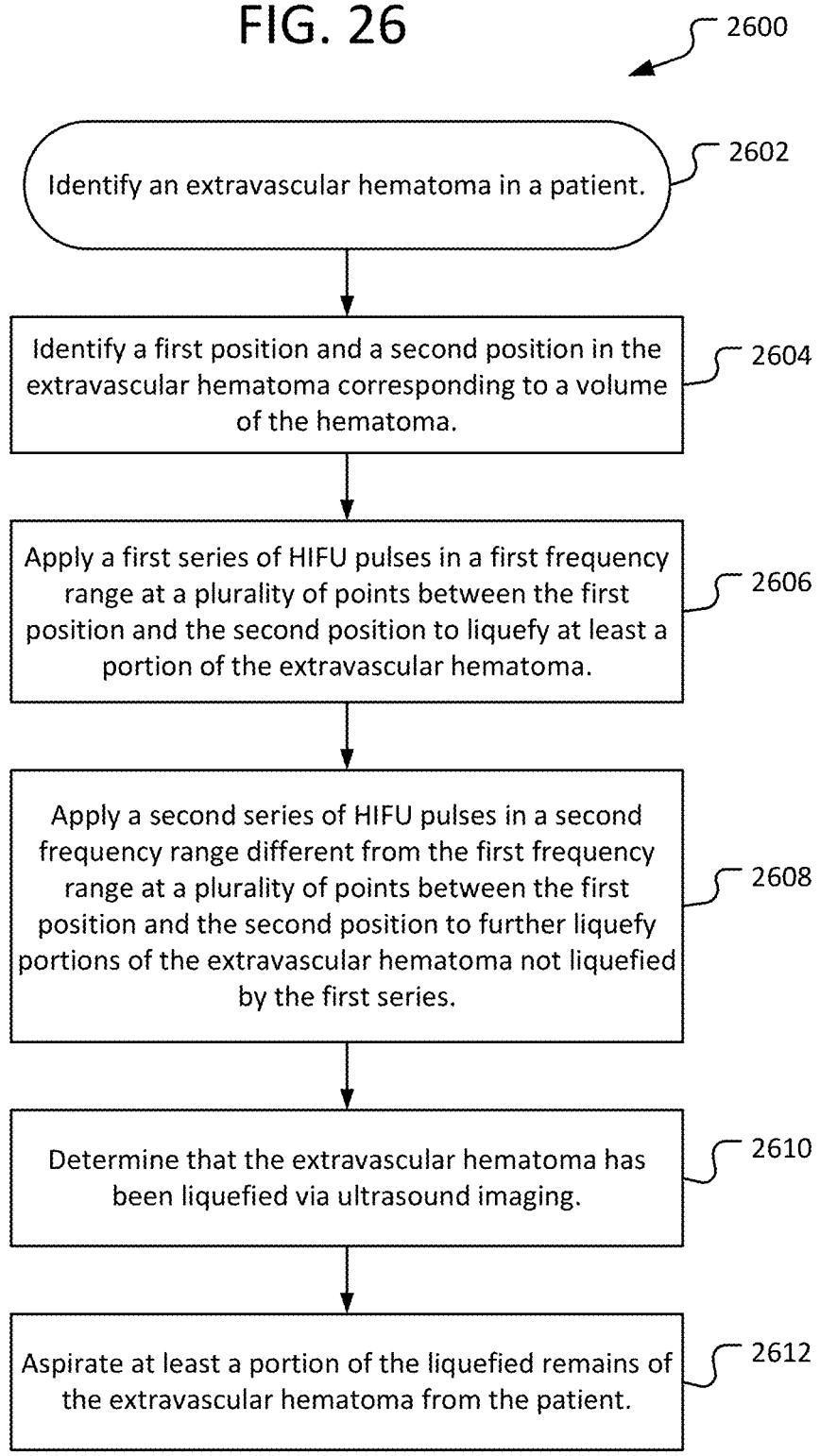

HISTOTRIPSY TREATMENT OF HEMATOMA

CROSS-REFERENCES TO RELATED APPLICATIONS

This application claims the benefit of priority to U.S. Provisional 62/239,751 filed Oct. 9, 2015, the contents of which are incorporated herein by reference for all purposes.

BACKGROUND

Extravascular hematomas are characterized by blood extravasation into the body. One form of extravascular hematoma is intramuscular hematoma, i.e. extravasation of blood into muscle tissue affected by trauma, with preserved integrity of the epimysium, e.g. in a limb. Significant limb hematomas occur in diverse populations, from professional athletes to amateur runners and exercise enthusiasts who sustain muscle injuries from repetitive overuse, as well as sharp and blunt limb trauma. The main symptom related to the onset of an intramuscular hematoma is pain, which may be debilitating. Extravascular hematomas are also possible elsewhere in the body, e.g. in and around the internal organs.

There are currently no short-term treatment options for large extravascular hematomas. Drainage of extravascular hematomas is generally difficult if not impossible because even large percutaneously placed drains are inefficient due to the firm gelatinous consistency of the hematomas. Conservative treatment includes rest, ice and compression, and the return to full activity is generally not possible before a period of 10-20 weeks. In addition, posttraumatic myositis ossificans—calcification of muscle—occurs as a complication in approximately 20% of large hematomas. It is responsible for considerable morbidity, with symptoms of prolonged pain, diminished flexibility, local tenderness and stiffness lasting an average of 1.1 years. One of the most devastating sequelae of large intramuscular hematomas is extremity compartment syndrome (ECS), which occurs when muscle tissues take on excess fluid (moderate to large hematoma or muscle swelling due to inflammation) creating pressure that reduces blood flow and ischemic injury. Increased pressures can cause irreversible damage over time, resulting from loss of vascular perfusion leading to loss of limb function/viability, in some cases requiring amputation.

A rapid, definitive intervention aiming at evacuation of the space-occupying hematoma would reduce pain, improve function, and avoid long term sequelae. Ultrasound is known to promote intravascular clot breakdown, as both a stand-alone procedure and used in conjunction with thrombolytic drugs and/or microbubbles. In-vitro and in-vivo studies have been conducted over the years, and acoustic cavitation is widely accepted as the dominant mechanism for mechanical disruption of the clot integrity and partial or complete recanalization of the vessel. Recently, a technique termed histotripsy that employs high-intensity focused ultrasound (HIFU) has been demonstrated to dissolve large in vitro and in vivo vascular clots without thrombolytic drugs within 1.5-5 minutes into debris 98% of which were smaller than 5 microns. However, this approach cannot be applied to the large extravascular hematomas due to their large volume (20-50 cc's) compared to intravascular clots, which necessitates much higher thrombolysis rates to complete the treatment within clinically relevant times (~15-20 minutes).

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Various embodiments herein described relate to apparatuses, systems, and methods for treating an extravascular hematoma in a patient. Methods can include applying a series of focused acoustic pulses to a respective series of focal points within the extravascular hematoma to liquefy at least a portion of the extravascular hematoma, and aspirating at least some of the liquefied portion of the extravascular hematoma from the patient. In some cases, the hematoma can be located by imaging ultrasound, e.g. transverse ultrasound. In some cases, the focused acoustic pulses have pulse durations in at least one of a first range and a second range, the first range being sufficiently long to generate a vapor bubble, and the second range being sufficiently short that focal heating does not create a vapor bubble. In some cases, the focused acoustic pulses have pulse durations in at least one of a first range and a second range, the first range being on the order of 1-50 ms, or in some cases 1-20 ms; and the second range being on the order of 3-50 μs, or in some cases 3-20 μs.

Applying the focused acoustic pulses can include a two-step process, including a debulking step and a liquefying step. The debulking step can include moving or scanning a focal region of a first series of focused acoustic pulses through a volume corresponding to the extravascular hematoma to quickly debulk the hematoma. The liquefying step can include moving or scanning a focal region of a second series of focused acoustic pulses through some portion of the volume of the hematoma corresponding to an unliquefied remainder of the extravascular hematoma after the debulking step. The first series can have HIFU parameters corresponding to long-H or boiling histotripsy (BH) methods, such that a relatively large volume is liquefied per treatment pulse. The second series can have HIFU parameters corresponding to short-H or cavitation histotripsy (CH) methods, such that smaller, albeit more regular, volumes can be disrupted by energetic cavitation bubble clouds at a finer degree of granularity than available from the BH methods. The step of moving the focal region of the first series of pulses through the volume can include emitting 1-20 pulses at each location of a plurality of locations in the first volume. In some cases, the liquefying step can include moving the focal region of the second series of focused acoustic pulses through a second volume corresponding to one or more non-hematoma features present in the extravascular hematoma.

Systems for treating an extravascular hematoma can include an acoustic emitter configured to emit high intensity focused ultrasonic energy, a sensor capable of detecting at least one of an ultrasound bubble cloud and a liquid pocket in a patient; and a processor and memory operable to control the system, in accordance with some embodiments. Such systems can cause the acoustic emitter to generate a first series of acoustic pulses to debulk at least a portion of the extravascular hematoma, and a second series of acoustic pulses to disrupt a nonliquid remnant of the extravascular hematoma. In some cases, systems can identify, by the sensor, a first volume corresponding to an interior region of the extravascular hematoma and a second volume corresponding to a periphery of the extravascular hematoma, cause the acoustic emitter to scan the first series of acoustic pulses through at least a portion of first volume to debulk the first volume; and cause the acoustic emitter to scan the second series of acoustic pulses through at least a portion of the second volume to disrupt remnants of hematoma. In some cases, systems for treating a hematoma can be configured to apply the first series of acoustic pulses at a duty cycle of 1-10%, pulse durations of 1-20 ms, and peak focal pressures of 70-100 MPa. The second series of acoustic pulses may be applied at pulse durations of 2-20 µs.

BRIEF DESCRIPTION OF THE DRAWINGS

Various embodiments in accordance with the present disclosure will be described with reference to the drawings, in which:

FIG. 26 illustrates a second example process for treating an extravascular hematoma in a patient, in accordance with embodiments.

DETAILED DESCRIPTION

Extravascular hematomas are a potential complication of injury, including sports injury, surgical injury, and other forms of trauma. Large limb hematomas are relatively common in sports injuries and lead to long layoffs for athletes and exercise enthusiasts. Standard conservative treatment of rest, ice, compression and elevation (RICE protocol) delays a return to full activity for a period of 10-20 weeks, and calcification complications in approximately 20% of large hematomas leads to prolonged reduction of use lasting an average of 1.1 years. An interventional technique that can rapidly and safely liquefy hematomas for fine needle aspiration could significantly reduce layoffs and allow return to full activities quickly.

Figure 1:
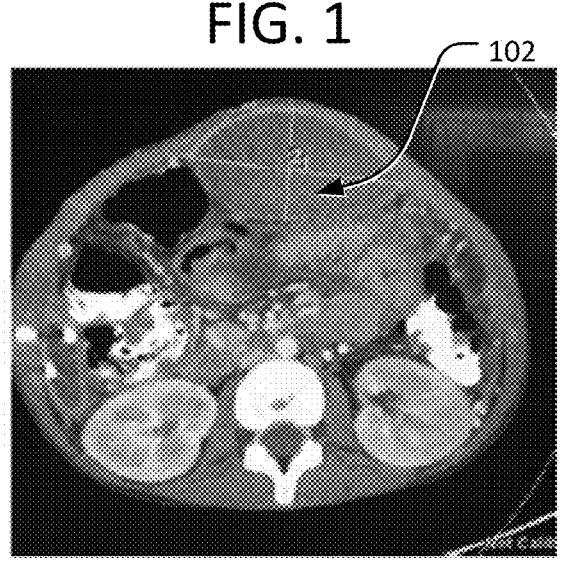
FIG. 1 shows a computerized tomography (CT) image of a large rectus sheathe extravascular hematoma.
Figure 2:
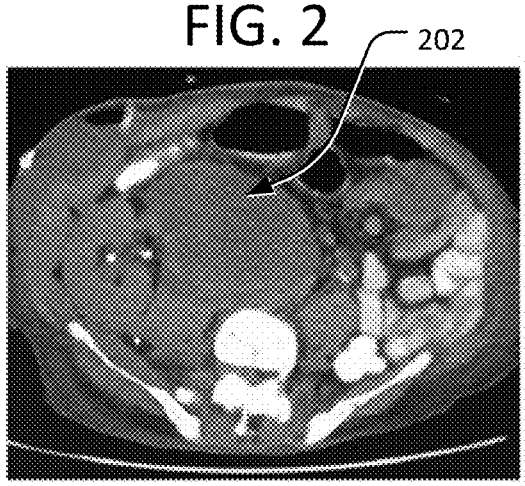
FIG. 2 shows a CT image of an extravascular hematoma around a transplanted kidney causing loss of renal function.
Figure 3:
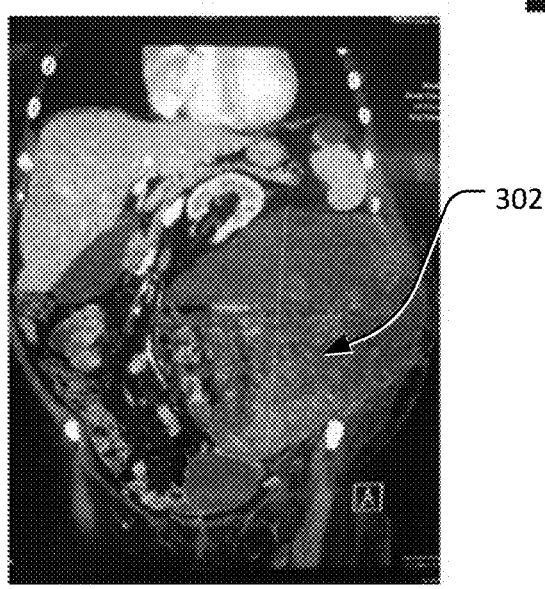
FIG. 3 shows a CT image of a large intraabdominal hematoma causing abdominal compartment syndrome.

By way of example, FIGS. 1-3 illustrate several large hematomas requiring immediate intervention. FIG. 1 shows a CT scan of a large, painful rectus sheathe extravascular hematoma 102. FIG. 2 shows a CT image of an extravascular hematoma 202 around a transplanted kidney causing loss of renal function. FIG. 3 shows a large intraabdominal hematoma 302 causing abdominal compartment syndrome. Each example has high associated morbidity and loss of function if treated surgically or by conservative techniques.

Systems and methods described herein provide for the application of histotripsy to liquefy large (e.g. up to 20 cc's, up to 30 cc's, or in some cases up to 100 cc's) in vitro hematomas. In extreme cases, an abdominal hematoma may take up most of the volume of the abdominal cavity (e.g. a liter or more), which can be addressed by methods described herein. The liquefaction of even large hematomas (e.g. 100 cc) can be achieved within clinically relevant timeframes (i.e., under 20 minutes). The liquid remnant of the liquefied hematomas (the lysate) can be subsequently aspirated from the void left by the hematoma using, e.g., a small needle on the order of 18 gauge, 21 gauge, or narrower. At the other extreme, small cosmetic hematoma (less than 1 cc) may be addressed by these methods.

Figure 4:
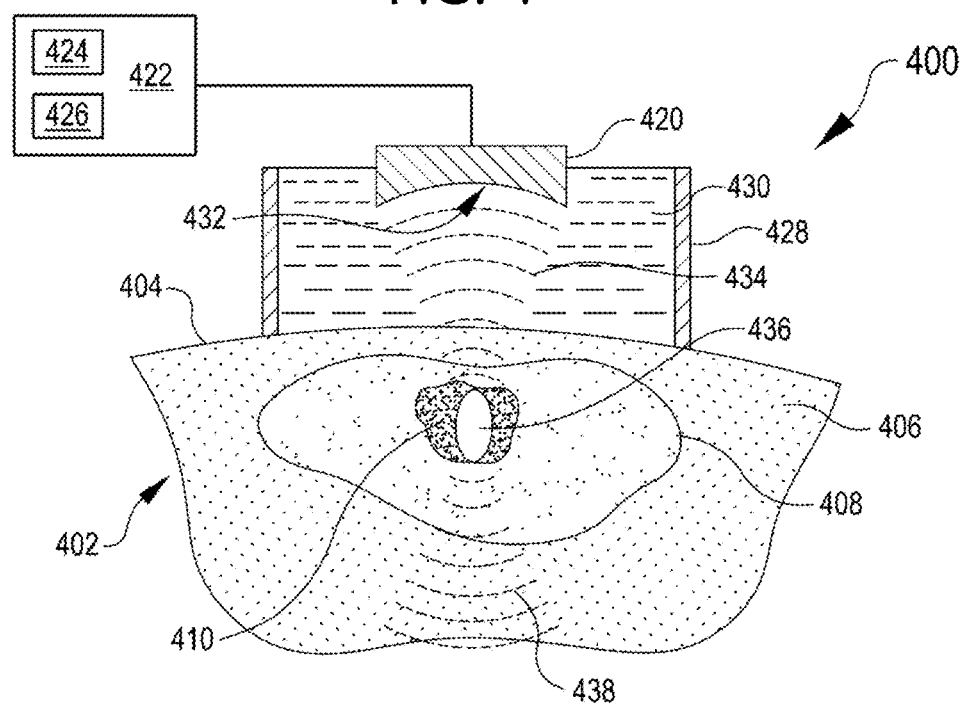
FIG. 4 is side cross-sectional schematic view illustrating a system for liquefying an extravascular hematoma in a patient, according to some embodiments of the present invention.

FIG. 4 illustrates a first example system 400 for treating an extravascular hematoma. The system 400 is positionable with respect to a patient 402 to target a hematoma 410 internal to the patient 402. In some cases, the hematoma 410 may also be internal to an organ 408. The hematoma 410 is separated from an exterior of the patient 402 by internal tissue 406 and skin 404.

The system 400 includes an acoustic emitter 420, which can be a high-intensity focused ultrasound (HIFU) emitter capable of emitting pulsed waveforms of high-intensity ultrasound toward a focus. The acoustic emitter 420 has an emitter face 432, which can include any suitable number of individual ultrasound transducers. The emitter face 432 can be oriented with respect to the patient 402 such that a focal region 436 of the ultrasound transducers thereon is positioned within the targeted hematoma 410.

The acoustic emitter 420 can be controlled by a computer 422, which may include one or more processors 424 and memory 426 that can store instructions to control the operation of the system 400. For example, the computer 422 can provide a signal to cause the acoustic emitter 420 to emit a suitable HIFU waveform for treating the hematoma, as described below. The computer 422 may also be operable to cause displacement of the acoustic emitter 420 with respect to the patient 402 in order to cause the focal region 436 to scan through a portion of the hematoma 410, so that a volume of the hematoma 410 can be liquefied.

The acoustic emitter 420 may be partially or fully immersed in an ultrasound-conductive medium 430 which can conduct ultrasonic energy without dissipating energy from the converging waveforms 434. The converging waveforms 434, as well as diverging, exiting waveforms 438 do not significantly interact with the patient 404 except at the focal region 436. In some cases, the medium 430 may be water or any other aqueous solution. In some cases, the medium 430 may be a gel. The medium may be contained within a frame 428, which can be aligned with the hematoma 410 and provide sufficient space for the acoustic emitter 420 to be moved so that the focal region 436 can be scanned throughout the hematoma 410. In some cases, the depth of the focal region 436 may be adjustable by changing a focal length of the acoustic emitter 420, such that the focal region of the acoustic emitter can be moved throughout the hematoma 410 without changing a distance between the emitter and the patient 402.

The acoustic emitter 420, in conjunction with the computer 422, can emit HIFU pulses to achieve liquefaction of the hematoma. The HIFU pulses can be emitted at a frequency range of between 1 MHz and 1.5 MHz, or in some cases between 1 MHz and 2 MHz. In some cases, a frequency range can be lower (e.g. for applications including deep hematomas), at about 0.6 MHz or lower; and in some cases, a frequency range can be higher (e.g. for applications including superficial or cosmetic hematomas), at up to 5 MHz or higher. The HIFU pulses can be delivered in at least two modes, including a long-duration ultrasound pulse ("long-H" mode) for inducing boiling histotripsy (BH), and a short-duration ultrasound pulse ("short-H" mode) for inducing cavitation histotripsy (CH).

The size of the histotripsy-induced cavities in soft tissue is known to decrease with frequency. Thus, for certain applications near the surface of the skin, e.g. cosmetic treatment of dermal or subdermal hematomas, frequencies up to 3 MHz may be used. However, both techniques described above require the formation of a shock front at the focus, and the fabrication of a transducer capable of achieving and sustaining output powers sufficient for that becomes increasingly difficult in the sub-MHz range.

The long-H mode, which induces boiling histotripsy (BH), involves the emission of targeted HIFU pulses at pulse durations of about 5-15 ms. In BH methods, nonlinear propagation effects between a transducer (such as the acoustic emitter 420) to the focal region lead to the formation of a shock front at the focus. Absorption and heating at the shock front is very large and leads to a highly-localized temperature rise of over 100° C. resulting in a boiling vapor bubble in only a few milliseconds. The explosion of the millimeter-sized boiling bubble and its further interaction with the shocks causes localized mechanical erosion of tissue at the focus. If the ultrasound pulse does not significantly exceed the time-to-boil and the duty factor is low enough to avoid heat buildup (below 2%), thermal injury to surrounding tissue is negligible.

A peak focal pressure for BH is about 70-100 MPa. The long-H, or BH mode, is operable to generate a bubble of trapped vapor within the extravascular hematoma (i.e., by boiling) which is suitable for debulking the hematoma. In particular, application of multiple BH pulses can rapidly debulk portions of the extravascular hematoma. The duration and frequency of application may also be expressed also in terms of a duty cycle, or "on" time per unit time, ranging from about 1-2%, or in some cases, from about 1-10%. The duty cycle and the pulse duration are limited by, e.g., the time required for heat to dissipate from the bubble of vapor without cooking or congealing the material of the hematoma or damaging any internal tissue or organs of the patient 402.

The short-H mode, which induces cavitation histotripsy (CH), involves the emission of targeted HIFU pulses at short pulse durations relative to the pulse durations for BH. In CH methods, the short (i.e. microsecond instead of millisecond) ultrasound pulses are emitted with high pressure amplitudes, and repeated with low duty factors, periodically producing dense energetic bubble clouds in tissue. The activity of the bubble clouds mechanically disintegrates tissue in the focal area to a subcellular level.

The CH pulses are operable to generate dense, targeted bubble clouds in tissue. By comparison with BH, the CH mode generates localized or "fine" disruption of hematoma material suitable to disrupt unliquefied remains of debulked hematomas, or to disrupt hematoma material near other tissue such as near blood vessels or organs adjacent to or passing through the hematoma. Both BH and CH modes described above are advantageously tissue selective, i.e., capable of liquefying hematomas without damaging connective tissue structures; and both modes are advantageously readily visible by scanning ultrasound techniques such as B-mode ultrasound.

Figure 5:
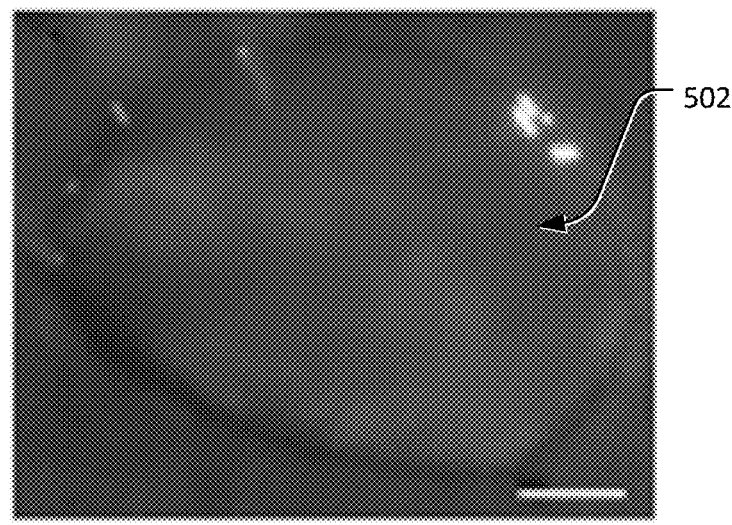
FIG. 5 is a gross view of a bisected histotripsy lesion induced in ex vivo bovine liver with liquefied contents.
Figure 6:
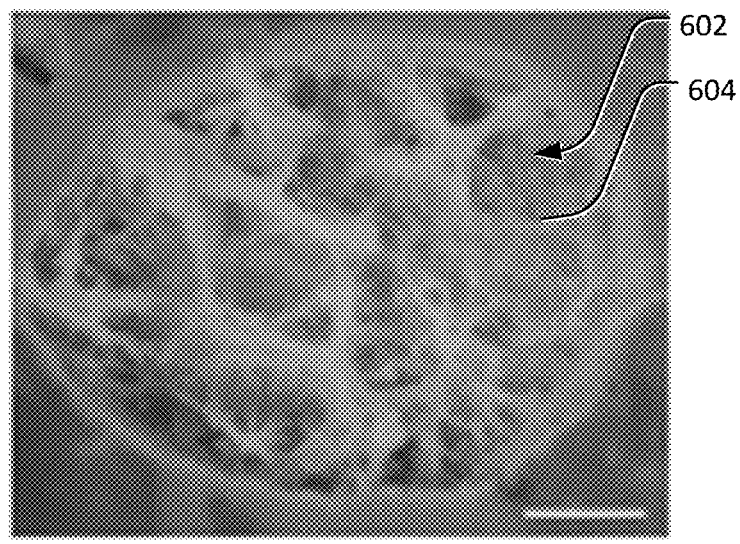
FIG. 6 shows the histotripsy lesion of FIG. 5 with the liquefied contents removed.

By way of example, FIG. 5 is a gross view of a bisected histotripsy lesion 502 induced in ex vivo bovine liver with liquefied contents. FIG. 6 is a gross view of the histotripsy lesion of FIG. 5 with the liquefied contents removed, showing voids 602 between intact connective tissue 604.

Figure 7:
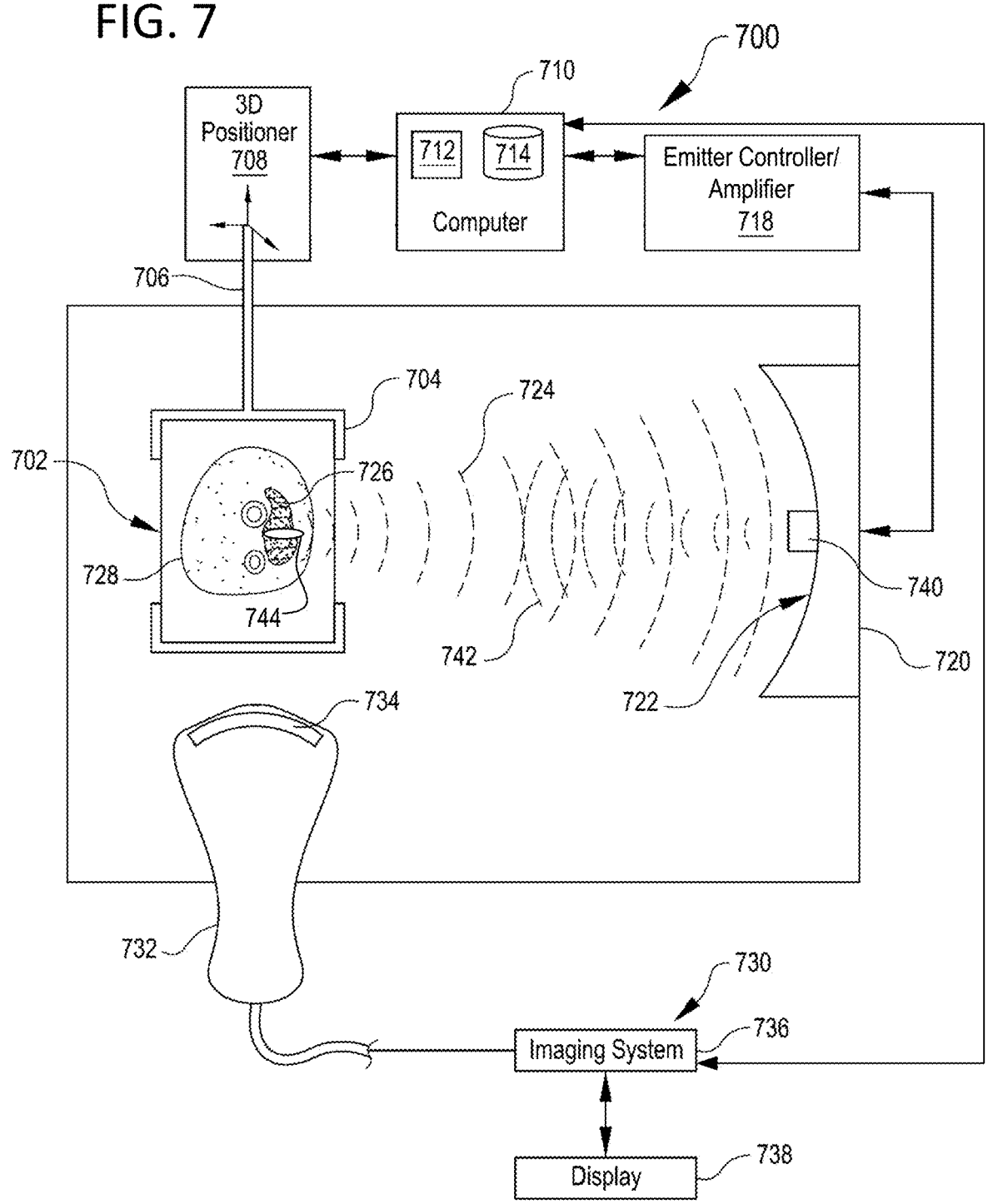
FIG. 7 is a cross-sectional schematic view illustrating another example system for liquefying an extravascular hematoma in a patient, in accordance with embodiments.

FIG. 7 illustrates another example system 700 for liquefying an extravascular hematoma 726 in a patient, in accordance with embodiments. The system 700 is shown with an acoustic emitter 720 positioned relative to a target 702 secured in a frame 704. It will be understood that, in some cases, the acoustic emitter 720 is movable with respect to the target 702 by way of, e.g., a 3D positioner 708. In other cases, the target 702 may be moved relative to the acoustic emitter 720. For example, the 3D positioner 708 may be connected with the frame 704 by way of a linkage 706 that permits the 3D positioner to translate the target 702 with respect to the emitter 720, or vice versa. The acoustic emitter 720 and target 702 may be immersed together in a container of medium, which in some cases may be degassed water.

The target 702, as shown, illustrates a body part (limb) 728 of a patient, in a cross-sectional view, showing a location of an extravascular hematoma 726. It will be understood that techniques herein described with reference to the system 700 may also be applied to any other suitable body part containing an extravascular hematoma.

The acoustic emitter 720 can be a HIFU emitter capable of emitting pulsed ultrasound waveforms 724, similar to the acoustic emitter 420 described with reference to FIG. 4. The acoustic emitter 720 has an emitter face 722 which can include any suitable number of individual ultrasound transducers. The emitter face 722 directs the HIFU waveforms 724 to a focal region 744 within the hematoma 726.

The acoustic emitter 720 and the 3D positioner 708 can operate under the control of a computer 710 having a processor 712 and non-transitory memory 714 that contain operating instructions for controlling the emitter and/or 3D positioner. The computer 710 may also communicate with an emitter controller and/or amplifier 718 which can generate and/or amplify waveforms for emission by the acoustic emitter 720 as the HIFU waveforms 724.

The system 700 may operate in conjunction with an imaging system 730 which can identify a position and shape of the extravascular hematoma 726 and a location of any boiling or cavitation bubbles produced within the hematoma by the HIFU waveforms 724. The imaging system 730 can include, e.g., an inline imaging transducer 740, a transverse imaging transducer 734, or a combination of the two. The imaging system 730 can include an imaging system controller 736, which can communicate with the computer 710 and with a display 738. In some cases, the imaging system 730 can exchange data with the computer 710 so that the computer can detect a position of the focal region 744 in the hematoma 726, and move the focal region to scan throughout a volume of the hematoma. The positioning of the acoustic emitter 720 relative to the target 702 can also be manipulated by hand by a user, e.g. based on visual feedback from the display 738. The inline or transverse imaging transducers 740, 732 may each be referred to generally as a sensor. The sensor or sensors can detect a position of the focal region of the ultrasound waveforms 724, e.g. by way of detecting an ultrasound bubble cloud in a patient; and can detect a liquid pocket in a patient formed after liquefaction of a hematoma, e.g. by detecting an anechoic region in the volume of the hematoma.

For example, the focal region 744 may be initially positioned by the system 700 at a position in the hematoma 726 proximal to the emitter 720, and then the focal region may be moved gradually into the hematoma toward a position distal from the emitter. In some cases, the computer 710 may control the 3D positioner to scan the focal region 744 throughout the hematoma 726 in a pattern to liquefy a portion of, or substantially all of, the hematoma. The computer 710 may also control the acoustic emitter 720 to selectively emit the HIFU waveforms 724 in a BH mode and/or a CH mode according to the position of the focal region 744 in the hematoma 726. For example, where the focal region 744 approaches a boundary of the hematoma 726, an inclusion, an internal structure, or any other internal feature, the acoustic emitter 720 may switch from using a BH mode to the CH mode. Preferably, the CH mode is used for disrupting and/or liquefying material at a fine degree of granularity compared to the BH mode, which is preferably used for debulking the hematoma.

Figure 8:
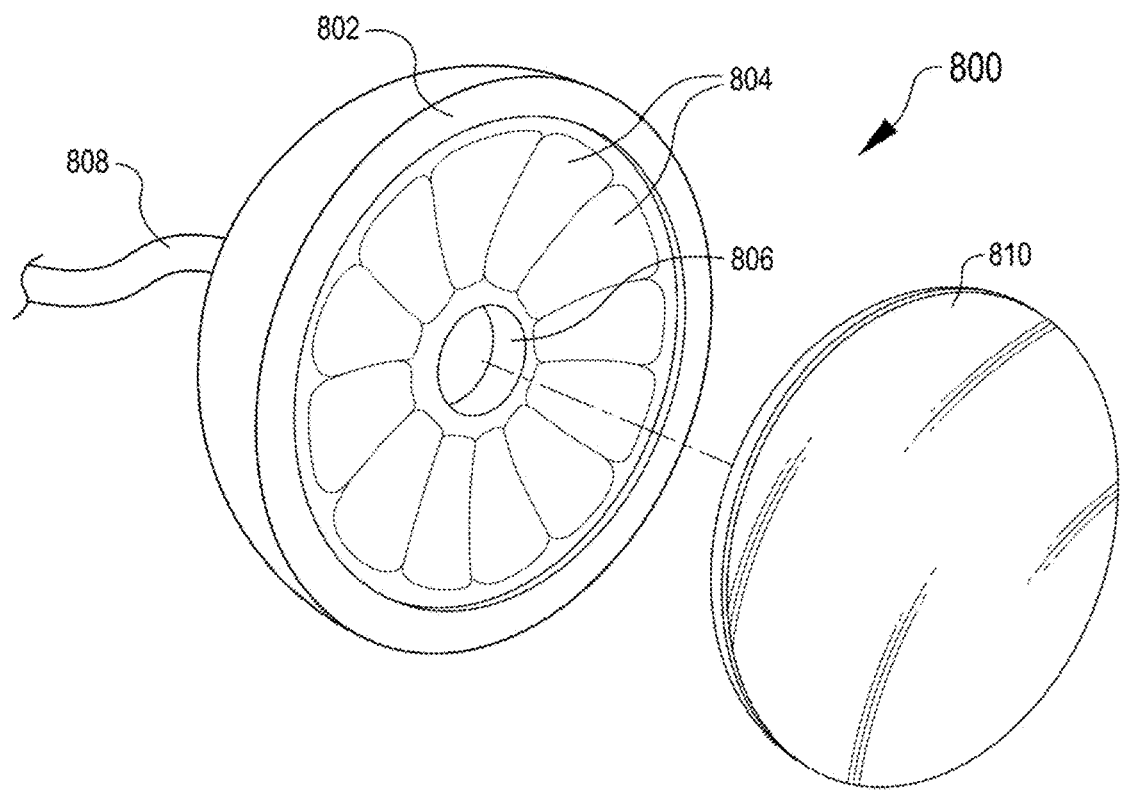
FIG. 8 is a perspective view of an example of an ultrasound emitter array for use in a system such as the systems shown in FIG. 4 and/or FIG. 7, in accordance with embodiments.

FIG. 8 is a perspective view of a first example of an acoustic emitter 800 for use in a system such as the systems 400, 700 shown in FIG. 4 and/or FIG. 7, in accordance with embodiments. The emitter 800 is in the form of an ultrasound array made up of multiple wedge-shaped ultrasound transducers 804 arrayed annularly within a casing 802. The transducers 804 can be arrayed on a plane, or can be oriented facing inward so that waveforms transmitted by the transducers meet at a common focus. In some cases, a central space 806 may be arranged to accept an in-line ultrasound imaging transducer, such as the inline transducer 740 (FIG. 7). A lens 810 may be positioned over the array of ultrasound transducers 804 in order to provide protection, e.g. fluid or impact protection without obstructing the energy from the ultrasound waveforms. The lens 810 may also be shaped to focus the ultrasound waveforms produced by the acoustic emitter 800, particularly if the ultrasound transducers 804 are arrayed on a plane. The emitter 800 may be connected to electronics, e.g. the computer 710 and/or controller/amplifier 718 (FIG. 7) by way of physical cabling 808, or by any other suitable means.

Figure 9:
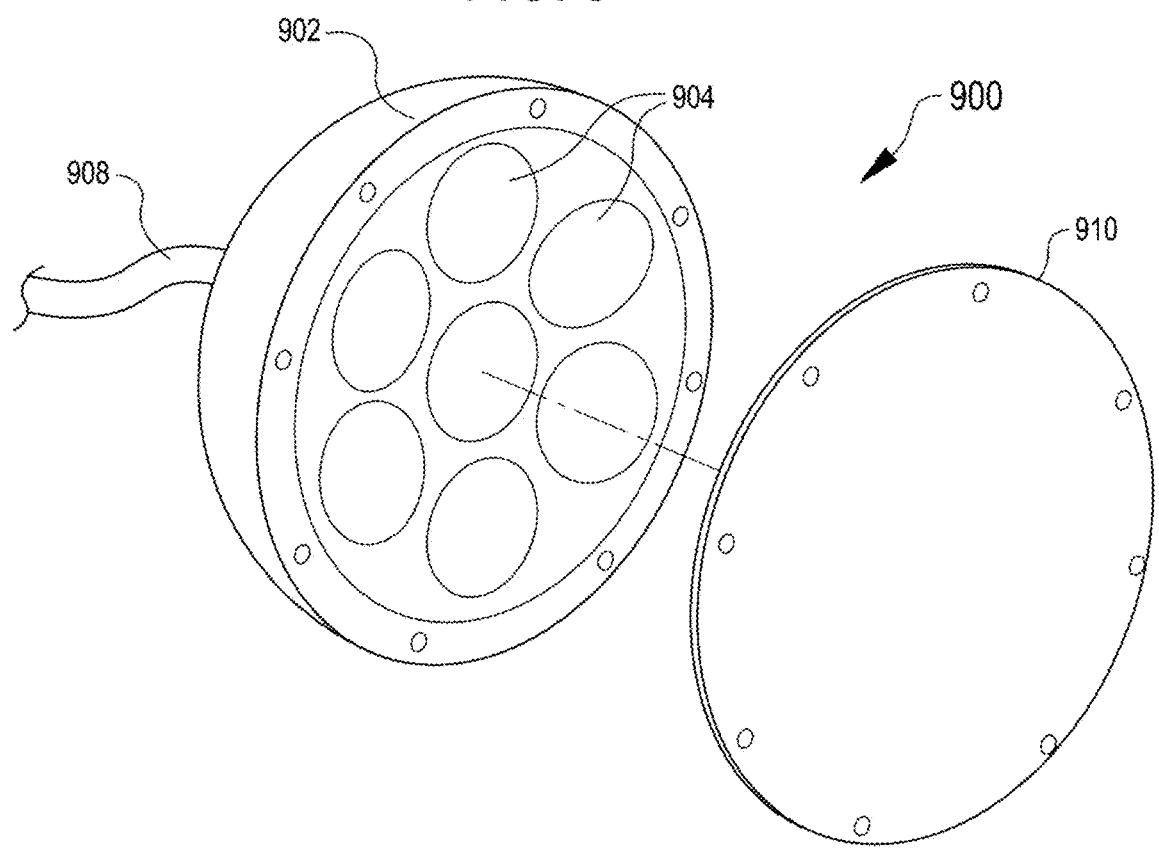
FIG. 9 is a perspective view of another example of an ultrasound emitter array for use in a system such as the systems shown in FIG. 4 and/or FIG. 7, in accordance with embodiments.

FIG. 9 is a perspective view of a second example of an acoustic emitter 900 for use in a system such as the systems 400, 700 shown in FIG. 4 and/or FIG. 7, in accordance with embodiments. The acoustic emitter 900 is in the form of an ultrasound array made up of multiple circular ultrasound transducers 904 arrayed in a pattern within a casing 902. The transducers 904 can be arrayed on a plane, or can be pointed inward so that the waveforms transmitted by the transducers meet at a common focus. In some cases, individual transducers 904 can each have a focal point coinciding with the common focus. The transducers 904 can be protected in some cases by a lens 910, which can be positioned to protect the transducers while transmitting ultrasound waveforms therethrough. The lens 910 may also be shaped to focus the ultrasound waveforms produced by the acoustic emitter 900, particularly if the ultrasound transducers 904 are arrayed on a plane. The emitter 900 may be connected to electronics, e.g. the computer 710 and/or controller/amplifier 718 (FIG. 7) by way of physical cabling 908, or by any other suitable means.

The systems 400, 700 described above with reference to FIGS. 4 and 7, and the emitters 800, 900 described with reference to FIGS. 8 and 9, are operable to emit pulsed HIFU waveforms according to one or both of the BH and CH modes described above. Example methods described herein were demonstrated experimentally according to the following parameters.

Experimental Methods:

The techniques described herein were demonstrating using BH and CH methods as described above, using the following specific protocols. The BH and CH modes were tested using 10 ms and 5-cycle pulse durations, at 1 Hz for BH and at 1000 Hz for CH. The peak focal pressures required to initiate bubble activity and thrombolysis in the two techniques were determined at each frequency, and were similar for CH and BH at 1 MHz, but were substantially higher for CH at 1.5 MHz. This was to be expected, because the threshold for inducing a cavitation cloud increases with frequency, whereas shock formation is not frequency dependent.

All experiments were performed using an in vitro model of a large hematoma. Fresh bovine blood obtained from a local butcher was poured into plastic molds (50 ml per mold) and allowed to clot at room temperature for 20 minutes. The resulting model hematomas (phantoms) were then transferred into a custom-built holder attached to a 3D positioning system similar to the 3D positioner 708 described in FIG. 7, and treated with BH, with CH, or with a combination treatment in a degassed water tank. Treatments were monitored via B-mode ultrasound (Epiq, Phillips, Bothell), with an imaging probe positioned in the tank perpendicular to the HIFU transducer axis. The position of the HIFU focus was determined with an initial pulse to generate a bubble, and marked on the ultrasound image before the start of the treatments. The focus was placed at 2 cm depth below the surface of the clot phantom. Two different spherically focused custom built transducers with an f-number of 1 were used in this study: a 12-element sector 1.5 MHz transducer with an aperture of 8 cm (similar to the emitter 800 shown in FIG. 8) and a 7-element 1 MHz transducer with an aperture of 12 cm (similar to the emitter 900 shown in FIG. 9). The transducers were manufactured from flat PZT-8 modules distributed on a flat surface and bonded by tungsten-epoxy matching layer to an acoustic lens manufactured with a stereolithography system following Kim et al., "Rapid prototyping fabrication of focused ultrasound transducers," *IEEE Trans Ultrason Ferroelectr Freq Control* 2014; 61(9), 1559-74, which is hereby incorporated by reference. The transducers were powered by a 2.5 kW custom built amplifier and an FPGA board controlled by a PC. It will be understood that the specific f-number used for applying focused ultrasound may vary depending on the depth of focus desired and the power output of the transducer. For example, suitable transducers may have an f-number varying from about 0.8 to 1.2, or in some cases, may have an f-number varying from about 0.5 to about 4.0. The desired f-number, and hence the selection of transducer, may vary depending on the specific application.

Figure 10:
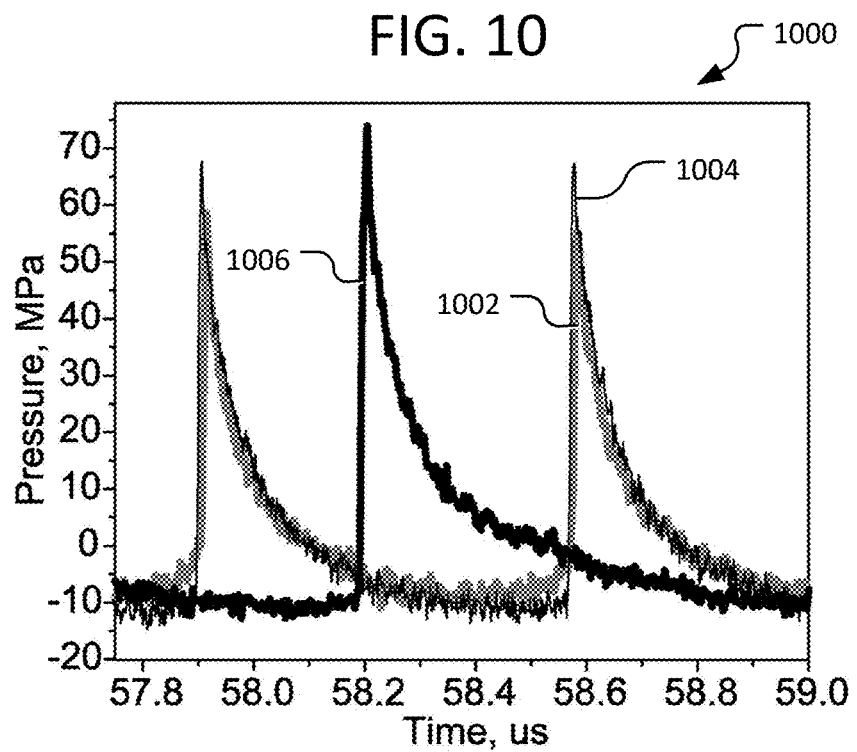
FIG. 10 is a chart graphically illustrating focal pressures of waveforms used for inducing liquefaction of extravascular hematomas in an experimental system similar to the systems shown in FIG. 4 and/or FIG. 7, in accordance with embodiments.

FIG. 10 is a chart graphically illustrating focal pressure waveforms used for inducing liquefaction of extravascular hematomas in an experimental system similar to the systems shown in FIG. 4 and/or FIG. 7, in accordance with embodiments. The focal pressures of the waveforms produced by the transducers at different output power levels were measured in water by a fiber optic probe hydrophone (FOPH 2000, RP Acoustics, Leutenbach, Germany). Measurements of the focal pressure of the waveforms are shown in FIG. 10 as a function of time. The focal pressure of the BH and CH waveforms at 1.5 MHz (1002, 1004 respectively) are shown compared to the focal pressure of the BH and CH waveforms at 1 MHz (1006, overlapping).

The waveforms were derated into the model clot material or phantom at 2 cm depth, using a derating algorithm developed for nonlinearly distorted waveforms, e.g. as described in Khokhlova et al., "Controlled tissue emulsification produced by high intensity focused ultrasound shock waves and millisecond boiling," *J Acoust Soc Am* 2011; 130(5), 3498-510, which is hereby incorporated by reference. The properties of clot material needed for derating were taken from the literature as follows: nonlinear parameter $\beta=4.15$, attenuation $\alpha=0.19$ Np/cm at 1 MHz and $\alpha=0.21$ Np/cm at 1.5 MHz. The derated waveforms corresponding to the output power used for BH and CH treatments are shown in FIG. 10.

In both CH and BH treatments, the pulse durations and the duty factors were kept constant throughout all exposures, and corresponded to the optimal parameters identified previously for soft tissue disintegration (for BH) or for intravascular clot lysis (for CH) as follows. BH treatments used 10 ms pulse durations at a pulse repetition frequency (PRF) of 1 Hz, resulting in 1% duty factor. CH treatments used 5-cycle pulses at a PRF of 1 kHz, resulting in 0.33-0.5% duty factor (for 1.5 MHz and 1 MHz frequencies, respectively).

The instantaneous output power of the transducer was set at the threshold level for initiating CH or BH treatment. That is, for BH, single 10 ms pulses with increasing output power were fired consecutively until a bright hyperechoic region was observed on B-mode ultrasound image. This derated focal waveform is shown in FIG. 10. The threshold peak focal pressures were $p^-=10$ MPa, $p^+=58$ MPa shock amplitude $A_s=64$ MPa at 1.5 MHz, and $p^-=12$ MPa, $p^+=82$ MPa and $A_s=64$ MPa at 1 MHz. These thresholds are in line with the theoretical estimations of the time to reach boiling, according to weak shock theory—6 ms and 4.3 ms for 1.5 MHz and 1 MHz, respectively. For CH methods, the 5-cycle pulses were fired at 1 kHz PRF while increasing the output power until a hyperechoic cavitation bubble cloud seen on B-mode ultrasound became stable. At 1 MHz the threshold output powers for both BH and CH methods were indistinguishable (see focal pressures 1006, FIG. 10); and at 1.5 MHz, the threshold output power for CH was higher than the threshold output power for BH (see focal pressure 1004 compared with focal pressure 1002, FIG. 10), corresponding to the peak focal pressures of $p^-=12$ MPa, $p^+=68$ MPa and $A_s=79$ MPa.

Experimental Results:

In a first series of experiments, BH or CH exposures of variable duration (5-60 seconds per location) were applied to separate focal spots in the hematoma phantom to evaluate the dose dependence of the liquefied void size. All the voids were contained within the gelatinous clot. The samples were then bisected along the axial dimension of the voids, and photographed for later analysis. In a second series of experiments, the focus was translated within the sample in a 2D rectangular grid, using 2-5 mm spacing between positions to cover a cross-sectional area of either 2×2 or 3×3 cm. An imaging transducer was then used to image the void and to guide a fine-needle (21-gauge) aspiration of the lysate from the void. The contents of the lysate were analyzed by histology and sized in a Coulter counter after filtering the entire collected volume through a 70-micron nylon filter.

Figure 11:
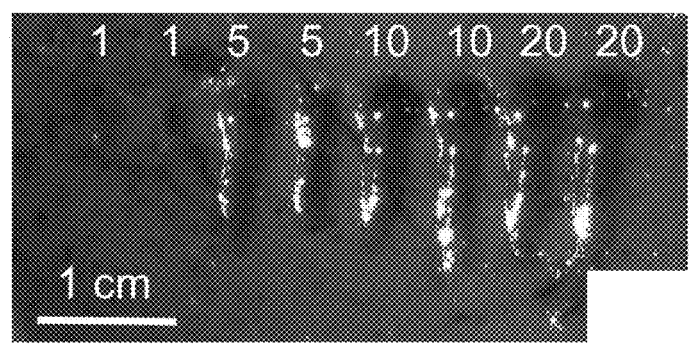
FIG. 11 is an image showing liquefied histotripsy lesions produced in a hematoma by long-duration ultrasound pulses (i.e. "long-H" or "BH" methods), in accordance with embodiments.
Figure 12:
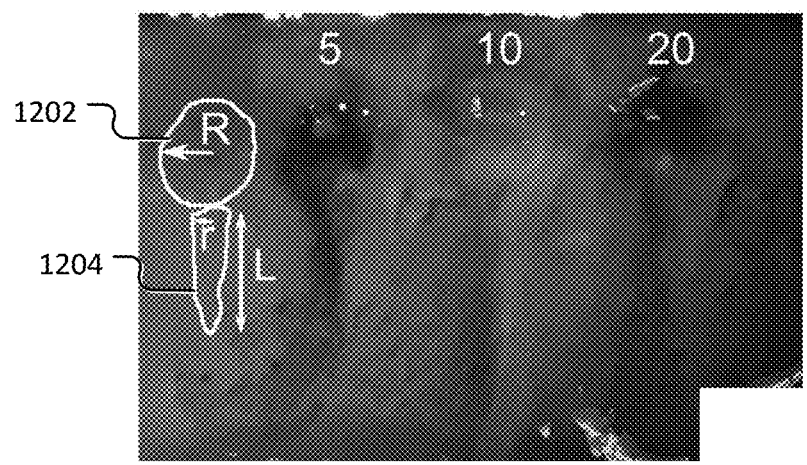
FIG. 12 is an image showing how volumes of the long-H lesions of FIG. 11 were calculated.

FIG. 11 shows representative examples of the gross appearance of individual BH lesions induced in the clot material at frequencies of 1 MHz and at 1.5 MHz, using variable exposure durations. These results were replicated at least three times in three different clot samples. As seen in FIGS. 11-12, long-H, or BH, lesions have a characteristic tadpole shape, and the linear dimensions of the lesion approach saturation relative to the exposure duration after only 10 seconds. The corresponding maximum linear dimensions at 1.5 MHz were 4.6 mm×13.4 mm, and at 1 MHz–22.6 mm×7.2 mm. To evaluate the liquefied volume achieved with each exposure, the lesions were represented as a combination of a sphere 1202 (the proximal part of the void) and a half-ellipsoid 1204 (the distal part of the void), as shown in FIG. 12. Volumes for BH lesions may thus be approximated based on the radius 'R' and half-ellipsoid long-axis 'L' according to Equation 1, below:

$$V = \frac{4}{3}\pi\left(\frac{LR^2}{2} + R^3\right) \quad \text{Equation 1}$$

Figure 13:
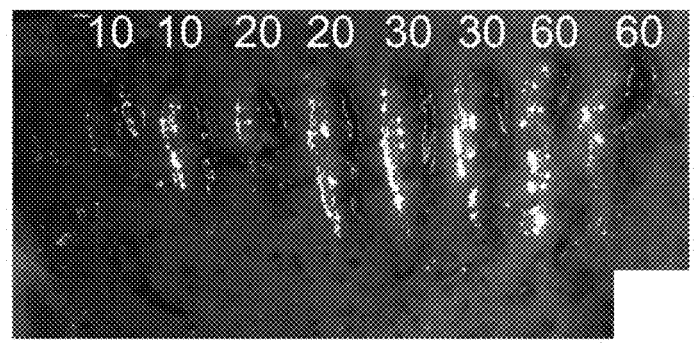
FIG. 13 is an image showing liquefied histotripsy lesions produced in a hematoma by short-duration ultrasound pulses (i.e. "short-H" or "CH" methods), in accordance with embodiments.
Figure 14:
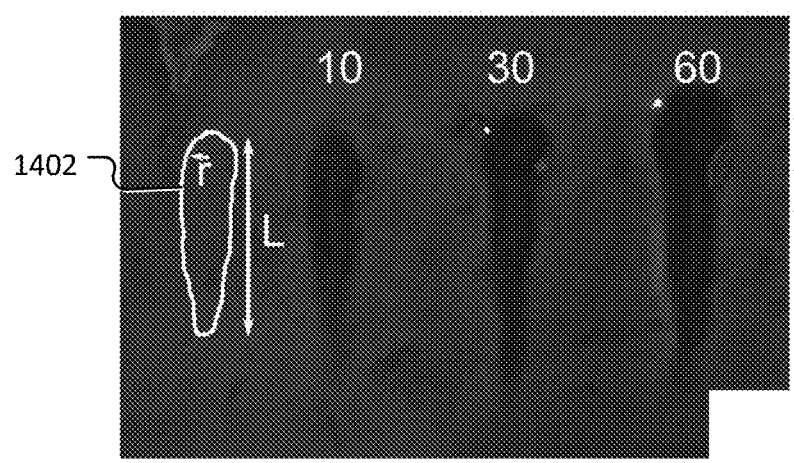
FIG. 14 is an image showing how volumes of the short-H lesions of FIG. 13 were calculated.

FIG. 13 shows representative examples of the gross appearance of individual CH lesions induced in the clot material at frequencies of 1 MHz and 1.5 MHz, also using variable exposure durations. As seen in FIGS. 13-14, CH lesions can be approximate led as an ellipsoidal volume, e.g. a 3-half ellipsoid with half-axes 'r' and 'L', as shown in FIG. 14 and according to Equation 2, below:

$$V = \frac{2\pi Lr^2}{3} \quad \text{Equation 2}$$

Figure 15:
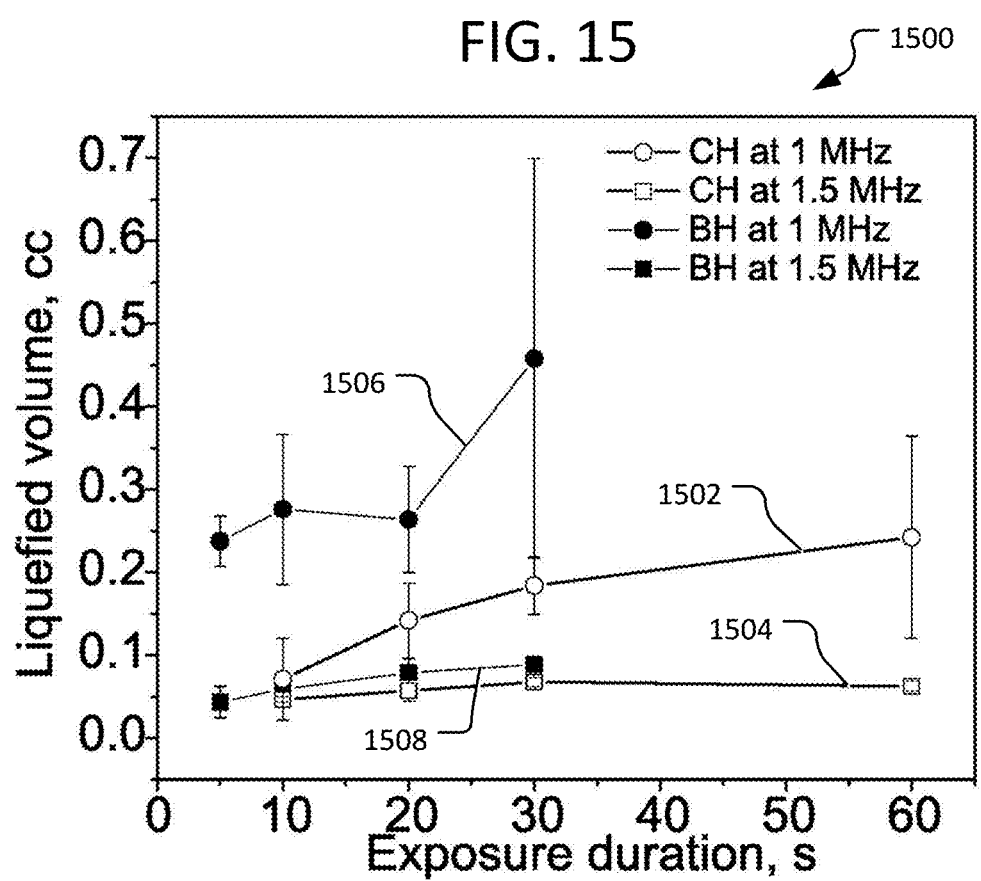
FIG. 15 is a chart graphically illustrating dependence of the estimated volume of long-H lesions and short-H lesions on waveform frequency and exposure duration.

FIG. 15 shows the corresponding dependence of the volume on the exposure duration and frequency. Each point on the curves in FIG. 15 can be used to estimate the upper limit of the thrombolysis rate per minute, given the liquefied volume achieved within the corresponding exposure duration and assuming that the same liquefaction volume will be achieved in consecutive focal points. Under these conditions the highest thrombolysis rate is achieved at an exposure duration of 5 s and is about 2.8 cc/min for 1 MHz and 0.5 cc/min for 1.5 MHz. Lesions produced by CH methods are substantially smaller than BH lesions produced in the same amount of time, but have a much more regular shape.

Figure 16:
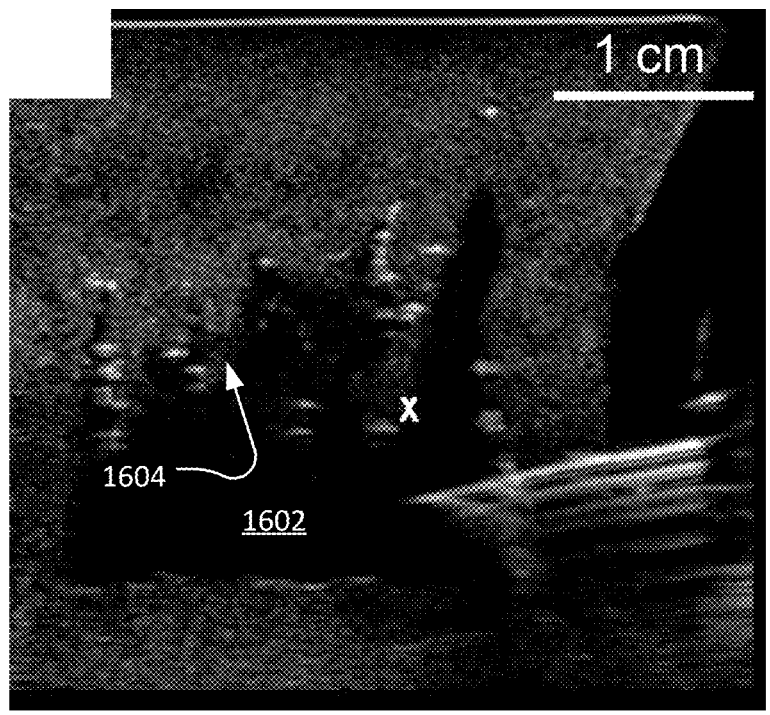
FIG. 16 is a B-mode ultrasound image showing a cavity produced by aspirating liquefied remains from a volumetric liquefied void in a hematoma liquefied by long-H methods.
Figure 17:
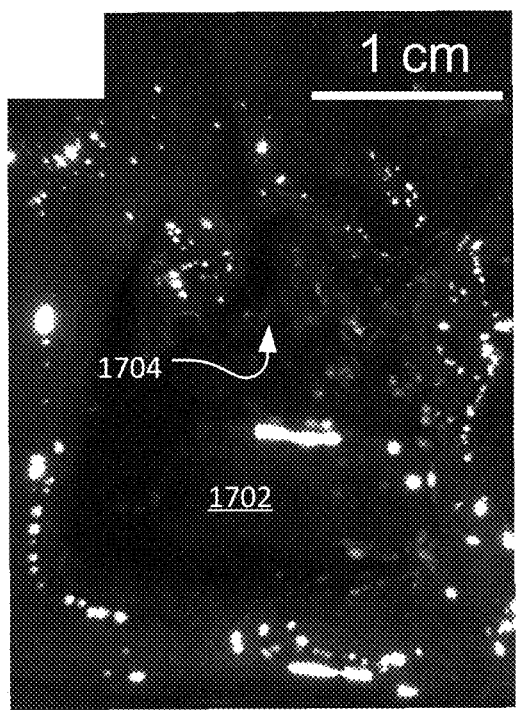
FIG. 17 is a photograph showing a bisected hematoma sample containing the volumetric liquefied void shown in FIG. 16.

The highest rate of thrombolysis was observed using BH for 5 s per location. However, the BH lesions have an irregular tadpole shape, and in order to achieve unobstructed fine-needle aspiration of a large-volume void, the individual lesions need to merge somewhat. In producing a large-volume void, two different lesion-placement strategies were used. In initial experiments, the 1.5 MHz transducer was used to produce lesions placed at 2-mm distance from each other. Exposure durations of 30 seconds per location were used to achieve merging of adjacent lesions. Thus, liquefaction of a 2×2 cm cross-sectional area took 50 minutes to complete. An imaging transducer was then used to guide fine-needle (21-gauge) aspiration of the lysate, as shown in FIG. 16. After 8 cc's of lysate was aspirated from the void, the sample was removed from the holder and bisected as shown in FIG. 17. The aspiration was somewhat hindered by the shape of the cavity—the presence of small, millimeter-sized filaments 1404 of intact clot protruding from the side of the void 1402 that was distal to the transducer during treatment. These filaments were caused by the tadpole shape of the individual lesions and their incomplete merging.

Figure 18:
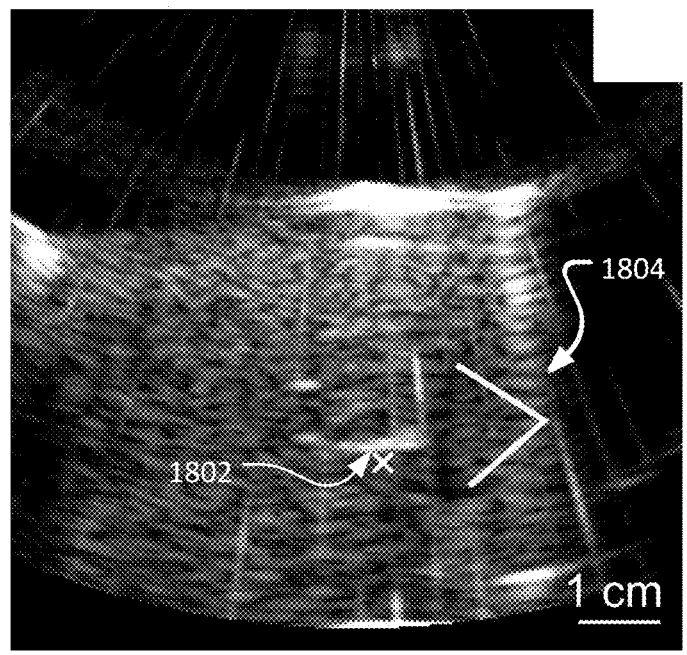
FIG. 18 is a B-mode ultrasound image showing a cavitation bubble cloud distal to merged liquefied voids produced by long-H methods.
Figure 19:
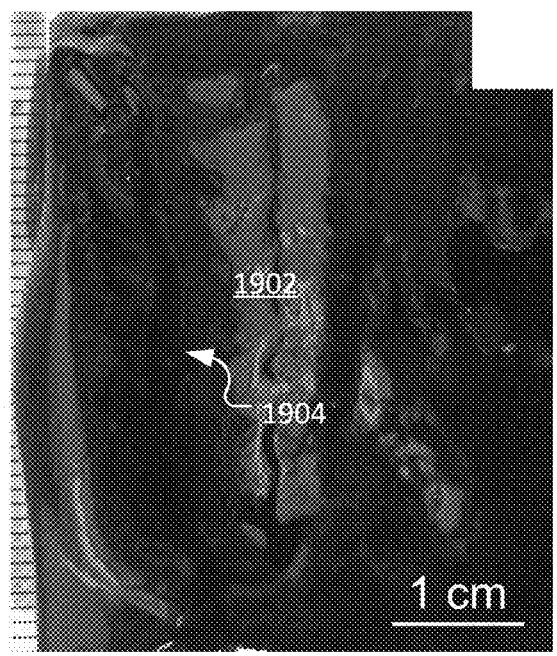
FIG. 19 is a photograph showing a bisected large void formed after combined treatment by long-H and short-H methods and subsequent drainage by aspirating liquid remains from the large void.

FIGS. 18-19 illustrate combined treatment with BH and CH methods using a 1 MHz transducer to accelerate liquefaction rate. FIG. 18 shows a B-mode image of a cavitation bubble cloud 1802 distal to the merged voids 1804 created by BH. FIG. 19 is a photograph showing a bisected large void 1902 after the combined treatment and drainage.

As illustrated in FIG. 18, The 1 MHz transducer was used to produce BH cavities with only 5 pulses, and the cavities were separated by 5 mm, so that only the proximal parts of the cavities merged. A cross-sectional area of 4×2 cm was treated in only 10.5 minutes. Treatment was then switched to the CH regime and applied to the distal parts of the lesions (i.e. at 1802, FIG. 18) to liquefy remaining filaments, so that fine-needle aspiration would not be hindered by the filaments. A rectangular pattern was used as for moving the focal region throughout hematoma sample in the BH regime, with 3-second exposures per spot, which overall took 7 minutes. Total treatment time was 17.5 min. Small needle (21-gauge) aspiration was then performed and 20 cc's of lysate were removed. The bisected sample (FIG. 19) shows a smooth side 1904, demonstrating that the proximal parts of the lesions were clearly merged and did not interfere with aspiration. This strategy amounted to an overall thrombolysis rate of 1.3 cc/minute, and is within a clinically relevant time frame (15-20 minutes) for an outpatient procedure. The smooth distal edge 1904 demonstrates that the regularity of lesions formed by the CH methods effectively eliminated filaments of the type that impact treatment using BH methods alone.

Figure 20:
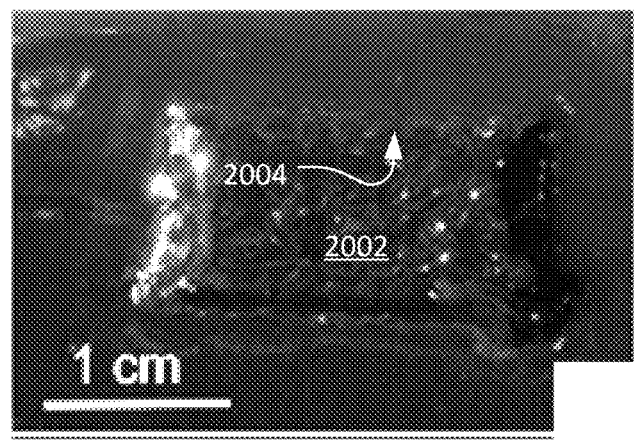
FIG. 20 is a photograph showing a bisected hematoma sample containing a cavity produced by aspirating liquid remains from a volumetric liquefied void produced by short-H methods.

FIG. 20 illustrates treatment of a hematoma sample using CH methods alone, showing an image of a void 2002 and a regular edge 2004 of the void produced in a model hematoma sample by CH methods using a 1.5 MHz transducer over a rectangular grid.

The examples above illustrate that both BH and CH histotripsy techniques induce transient bubble activity in the focal area of the transducer, and lead to the outcome of tissue liquefaction. In both techniques, reliable treatment monitoring is achieved by B-mode ultrasound imaging of the highly reflective bubbles that appear as bright hyperechoic regions. Furthermore, both techniques have previously demonstrated advantageous tissue selectivity, both in vivo and ex vivo: for example, connective tissue structures (e.g. blood vessels, biliary structures) proved to be very resistant to mechanical damage and were largely unaffected by BH treatment while the more fragile cellular components were completely lysed.

One notable difference between BH and CH methods is that the individual lesions produced by BH are larger than those produced by CH for the same treatment time, using the same ultrasound frequency. On the other hand, a unique feature of CH techniques is the formation of fluid vortices adjacent to the bubble cloud that were shown to attract, trap and erode millimeter-sized thrombus fragments if induced in a large blood vessel. Thus, a combination of BH (for large-scale debulking of a large hematoma) and CH (for eroding residual fragments) would optimize liquefaction treatment times for large extravascular hematomas. In this work CH, BH and a combination thereof were investigated in an in vitro model of a large hematoma in an effort to maximize the rate of thrombolysis for subsequent fine-needle aspiration.

In practice, the specific quantities of material that are liquefied by BH methods and by CH methods can vary depending on the geometry of the hematoma, the size of the hematoma and its location in the body, and other factors. For example, in some cases, the debulking step (BH methods) may liquefy about 50% of the hematoma, and the liquefying step (CH methods) may liquefy a remainder comprising about 50% of the hematoma by volume. However, in some cases, the debulking step can liquefy up to about 95% of the material of the hematoma, and the liquefying step can treat the remaining 5%. In general, the ratio of material liquefied by the debulking and liquefying steps may be approximately about 80/20%.

Figure 21:
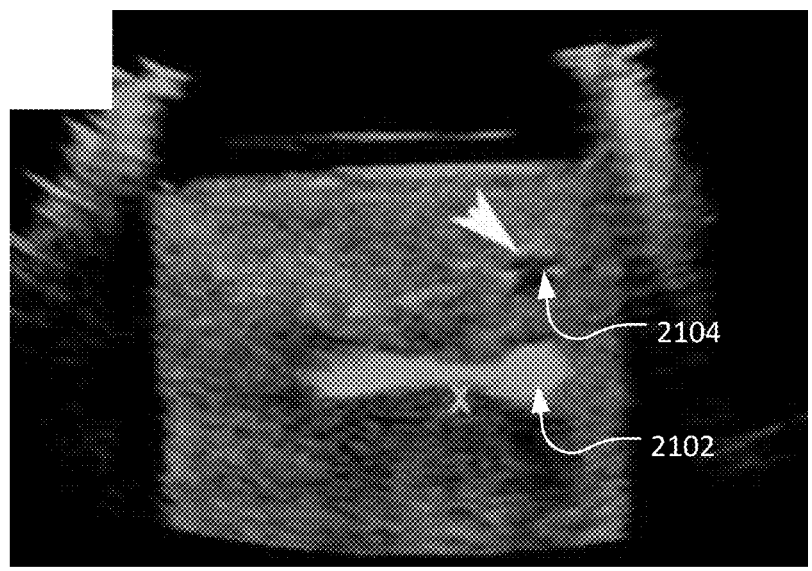
FIG. 21 is a B-mode ultrasound image showing bubble activity and hyperechoic regions corresponding to voids in a hematoma produced by treatment using long-H methods.
Figure 22:
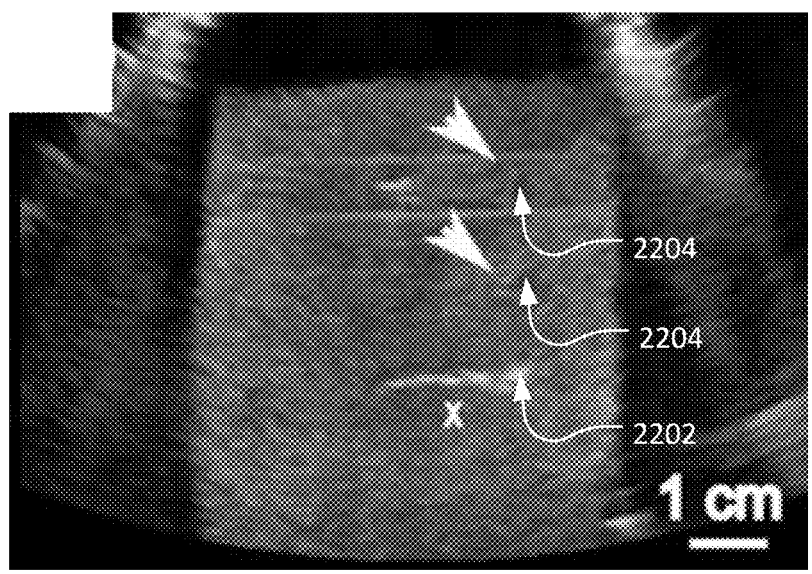
FIG. 22 is a B-mode ultrasound image showing bubble activity and hyperechoic regions corresponding to voids in a hematoma produced by treatment using short-H methods.

Examples of the B-mode images recorded during BH and CH exposures at 1 MHz are presented in FIGS. 21 and 22, respectively. The hematoma phantom is mildly hyperechoic, which is consistent with the appearance of a fresh clot as well as organized hematoma and represents the irregular fibrin matrix. The bright hyperechoic regions 2102, 2202 represent the areas of either bubble activity originating from boiling (FIG. 21) or the cavitation cloud (FIG. 22). A few seconds after the exposure is finished, all the residual bubbles dissolve leaving behind hypoechoic areas 2104, 2204 corresponding to the resulting voids, indicating that the fibrin matrix in that area is mechanically destroyed and the contents liquefied.

Figure 23:
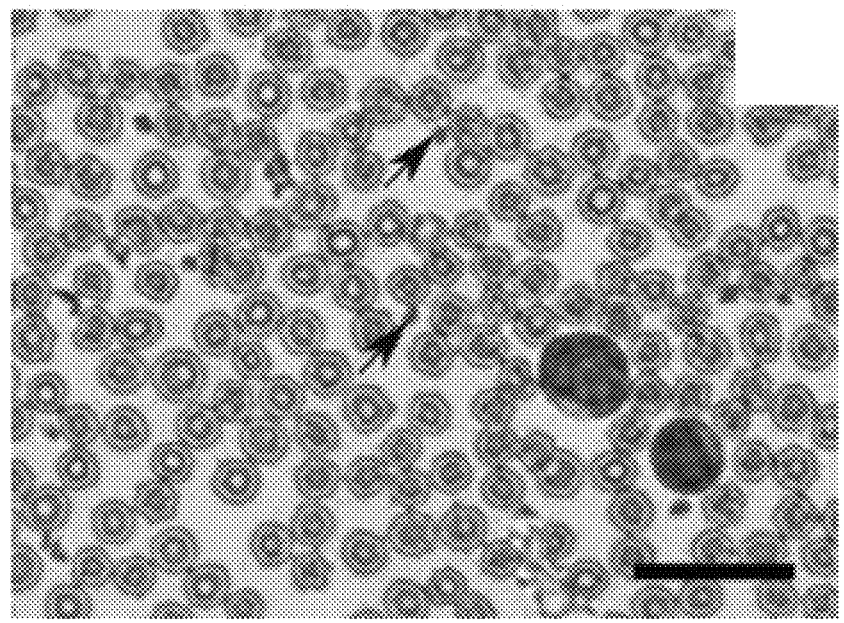
FIGS. 23 and 24 show histological slides illustrating aspects of the clot fragments extracted from liquefied voids in hematomas.
Figure 24:
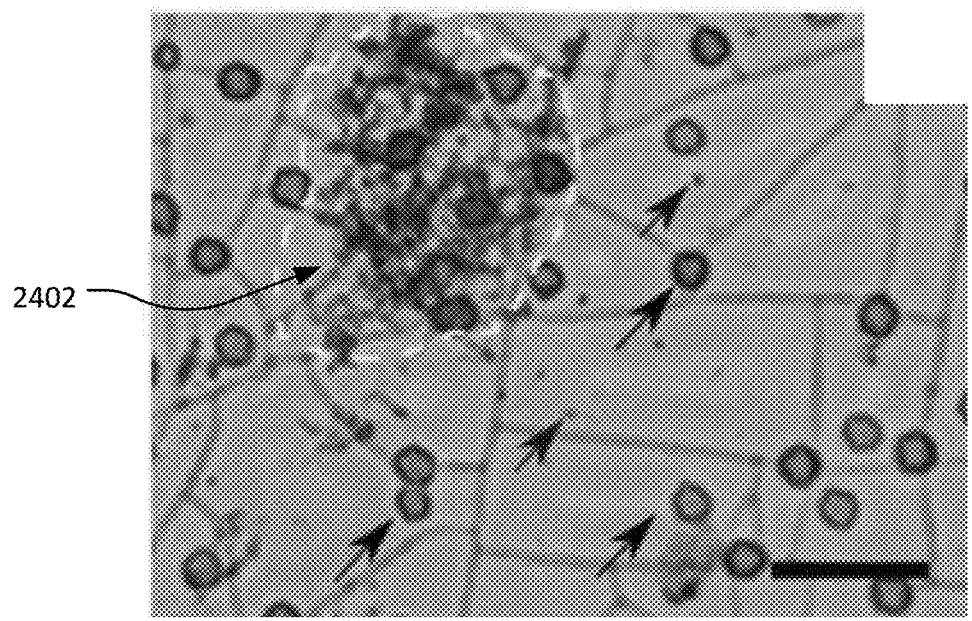

Analysis of the Lysate:

FIGS. 23-24 show histological slides illustrating aspects of the clot fragments extracted from liquefied voids in hematomas. Smears of the lysates aspirated from the large-volume voids were analyzed histologically using Wright-Giemsa stain and compared to a smear of untreated, non-coagulated bovine blood (FIG. 23). Regardless of the method employed for clot lysis, the lysate contents were very similar. Some intact red blood cells were detected, although intense background indicated a higher degree of hemolysis compared to the untreated blood. Few larger particulates containing red blood cells embedded into what appeared as fibrin matrix residuals ranging within 10-25 microns in size were seen on some histological slides (see example matrix 2402 in FIG. 24). However, these residual clot fragments did not hinder fine-needle aspiration. According to the sizing of the samples of the aspirated volume by Coulter Counter, no debris were larger than 25 microns, and 99% of the particles were smaller than 10 microns, likely representing intact RBCs.

Figure 25:
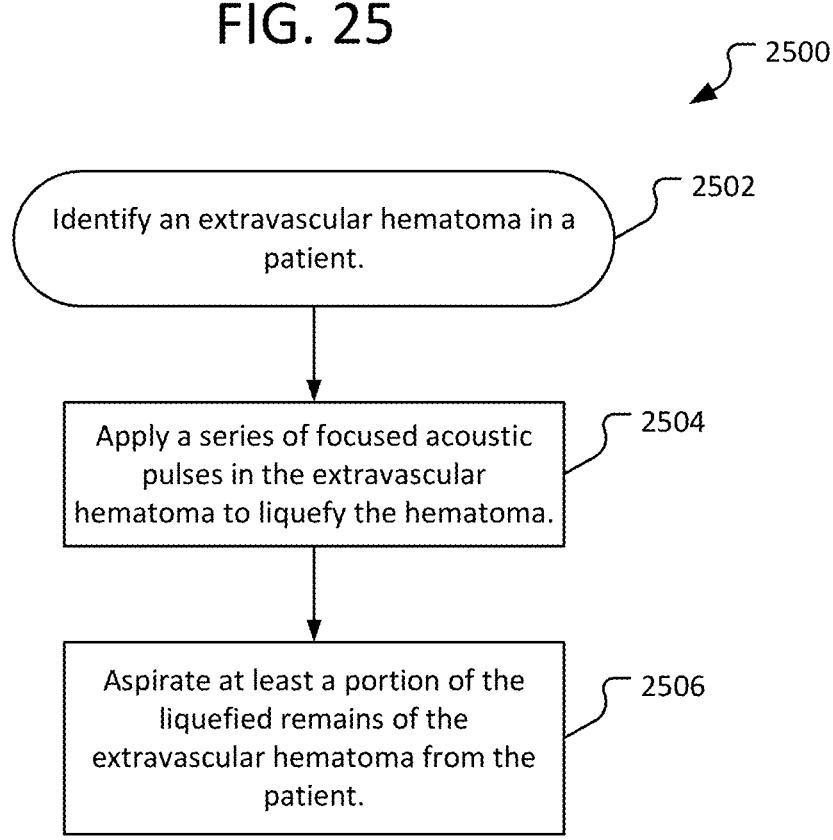
FIG. 25 illustrates a first example process for treating an extravascular hematoma in a patient, in accordance with embodiments.

FIG. 25 illustrates a process 2500 for treating an extravascular hematoma in a patient using a system similar to systems 400 or 700 described above with reference to FIGS. 4 and 7, in accordance with embodiments. In an embodiment, the process 2500 includes identifying an extravascular hematoma in a patient (act 2502). The hematoma may be identified, for example, by use of imaging ultrasound. A series of focused acoustic pulses can be directed into the extravascular hematoma to liquefy the hematoma (act 2504). Applying the focused acoustic pulses can include applying a HIFU waveform at a focal region that liquefies the hematoma near the focus by BH methods, CH methods, or a combination of both. The focal region of the series of focus acoustic pulses can be scanned through a volume of the extravascular hematoma to liquefy any portion, or substantially all of a volume of the hematoma. Once the extravascular hematoma is liquefied, the liquefied remains of the hematoma can be aspirated from the void left by the hematoma, e.g. using a needle or other suitable drainage device (act 2506). In some cases, the process can be performed at thrombolysis rates of at least 0.5 cc/min, 1.8 cc/min, or more than 2.5 cc/min.

FIG. 26 illustrates a second process 2600 for treating an extravascular hematoma in a patient using a system similar to systems 400 or 700 described above with reference to FIGS. 4 and 7, in accordance with embodiments. In an embodiment, the process 2600 includes identifying an extravascular hematoma in a patient (act 2602). A first position and a second position may be further identified in the hematoma (act 2604). In some cases, the first and second positions can correspond to a volume of the hematoma, or corresponding to a pattern configured to facilitate liquefaction of at least a portion of the hematoma. For example, a grid-shaped pattern may be identified for treating substantially all of the volume of the hematoma. A first series of HIFU pulses can be applied by an acoustic emitter at a range of positions between the first and second positions corresponding to at least a portion of the hematoma (act 2606). In some cases, the first series of HIFU pulses can include a BH waveform pattern configured to substantially debulk the hematoma. A second series of HIFU pulses can be applied by an acoustic emitter at another range of points within the first and second positions corresponding to at least another portion of the hematoma (act 2608). In some cases, the second series of HIFU pulses can include a CH waveform pattern configured to eliminate remnants left behind by the debulking phase (e.g. filaments of material not liquefied by the BH methods). The second series of HIFU pulses can be routed along interstices between the volumes affected by the first series of HIFU pulses, can trace boundaries of the volume of the hematoma, or can be applied in proximity to tissues or structures that were avoided by the first series of pulses. The positioning of each of the first and second series of HIFU pulses can be continuously or periodically monitored by way of imaging ultrasound. For example, in some cases, as each site in the extravascular hematoma is liquefied, the liquefaction of the site can be assessed by sensing an anechoic region at the site. The focal region for the HIFU pulses can then be moved to an adjacent site outside the anechoic region to continue liquefying the hematoma, and the process can be repeated until the entire extravascular hematoma is liquefied. The complete liquefaction of the targeted extravascular hematoma can be verified by imaging ultrasound (act 2610). Once liquefied, the extravascular hematoma can be removed by aspiration, e.g. with a needle or drain, from the patient (act 2612).

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

What is claimed is:

1. A method for treating an extravascular hematoma in a patient, the method comprising:
   applying a first series of focused acoustic pulses to debulk a first volume corresponding to an interior of the extravascular hematoma by moving a focal region of the first series of focused acoustic pulses through the first volume;
   after debulking the first volume, applying a second series of focused acoustic pulses to liquefy a second volume of the interior of the extravascular hematoma by moving a second focal region of the second series of focused acoustic pulses through the second volume, the second volume comprising an unliquefied remainder of the extravascular hematoma; and
   monitoring a first position of the first focal region of the first series of focused acoustic pulses by detecting one or more bubbles induced by the first series of focused acoustic pulses or monitoring a second position of the second focal region of the second series of focused acoustic pulses by detecting one or more bubbles induced by the second series of focused acoustic pulses;
   determining that the extravascular hematoma is liquefied at the first position by detecting one or more anechoic regions in the extravascular hematoma at the first position;
   repositioning the first focal region or second focal region of focused acoustic pulses based in part on detecting the one or more anechoic regions; and
   determining a suitable aspiration site for aspirating a liquefied portion of the extravascular hematoma based in part on detecting the one or more anechoic regions; and
   aspirating at least some of the first and second volumes of the extravascular hematoma from the patient.

2. The method of claim 1, further comprising:
   locating the extravascular hematoma by transverse ultrasound.

3. The method of claim 1, wherein the first series of focused acoustic pulses comprise first pulse durations in a first range that is sufficiently long to generate a vapor bubble, and the second series of focused acoustic pulses comprise second pulse durations in a second range that is sufficiently short that focal heating does not create a vapor bubble.

4. The method of claim 1, wherein moving the first focal region through the first volume comprises emitting the focused acoustic pulses at each location of a plurality of locations in the first volume until the extravascular hematoma at each location is debulked.

5. The method of claim 1, wherein:
   applying the second series of focused acoustic pulses comprises moving a focal region of the second series of focused acoustic pulses through a third volume corresponding to one or more non-hematoma features present in the extravascular hematoma.

6. The method of claim 1, wherein particulates contained in the first and second volumes after application of the first series and second series of focused acoustic pulses are sufficiently small to be aspirated without clogging a needle.

7. The method of claim 1, wherein the first series of focused acoustic pulses have pulse durations in a first range comprising 1-50 ms, and the second series of focused acoustic pulses have pulse durations in a second range comprising 3-50 µs.

8. The method of claim 1, wherein:
   each pulse of the first series of focused acoustic pulses is characterized by a first frequency range of 0.6 to 5 MHz and a first duration sufficiently long to generate a vapor bubble; and
   each pulse of the second series of focused acoustic pulses is characterized by a second frequency range of 0.6 to 5 MHz and a second duration sufficiently short that focal heating does not create a vapor bubble.

9. A system for treating an extravascular hematoma in a patient, the system comprising:
   an acoustic emitter configured to emit high intensity focused ultrasonic energy in a series of focused acoustic pulses, the focused acoustic pulses having pulse durations in at least one of a first range and a second range, the first range being sufficiently long to generate a vapor bubble; and the second range being sufficiently short that focal heating does not create a vapor bubble;
   a sensor configured to detect ultrasound reflection; and
   a processor and a memory containing instructions, the instructions operable to cause the processor to:
      cause the acoustic emitter to generate a first series of acoustic pulses having durations in the first range, the first series being configured to debulk a first volume corresponding to an interior of the extravascular hematoma by moving a focal region of the first series of focused acoustic pulses through the first volume; and
      cause the acoustic emitter to generate a second series of acoustic pulses having durations in the second range, the second series being configured to liquefy a nonliquid remnant of the extravascular hematoma, by moving a second focal region of the second series of focused acoustic pulses through a second volume, the second volume comprising an unliquefied remainder of the extravascular hematoma;
      monitor a first position of the first focal region of the first series of focused acoustic pulses by detecting, via the sensor, one or more bubbles induced by the first series of focused acoustic pulses or monitor a second position of the second focal region of the second series of focused acoustic pulses by detecting, via the sensor, one or more bubbles induced by the second series of focused acoustic pulses;
      determine that the extravascular hematoma is liquefied at the first position by detecting, via the sensor, one or more anechoic regions in the extravascular hematoma at the first position;
      repositioning the first focal region or second focal region of focused acoustic pulses based in part on detecting the one or more anechoic regions; and
      determine a suitable aspiration site for aspirating a liquefied portion of the extravascular hematoma based in part on detecting the one or more anechoic regions.

10. The system of claim 9, wherein the instructions are further operable to cause the processor to:
    identify, by the sensor, the first volume of the extravascular hematoma corresponding to a region for debulking; and
    identify, by the sensor, the second volume of the extravascular hematoma corresponding to the nonliquid remnant.

11. The system of claim 9, wherein the instructions are further operable to cause the processor to:
  identify, by the sensor, the first volume corresponding to an interior region of the extravascular hematoma and a third volume corresponding to a non-hematoma feature in the extravascular hematoma; and
  cause the acoustic emitter to scan a third series of acoustic pulses through at least a portion of the third volume.

12. The system of claim 11 wherein the non-hematoma feature comprises one of a vascular structure, a bone, a muscle, a calcification, or an organ.

13. The system of claim 9, wherein the acoustic emitter comprises a wide band emitter having a total frequency range of at least 0.3-5.0 MHz.

14. The system of claim 9, wherein the first series of acoustic pulses is applied at first pulse durations comprising 1-50 ms, and the second series of acoustic pulses is applied at second pulse durations comprising 3-50 µs.

15. The system of claim 9, wherein a peak focal pressure of the focused acoustic pulses is sufficient to cause a vapor bubble for pulse durations between 1-50 ms and sufficient to create cavitation without causing the vapor bubble for pulse durations between 3-50 µs.

16. The system of claim 9, wherein the first series of acoustic pulses is applied at a first duty cycle of 1-10% and the second series of acoustic pulses is applied at a second duty cycle of 0.1-0.5%.

17. The system of claim 9, wherein each pulse of the first series of acoustic pulses and each pulse of the second series of acoustic pulses are focused according to an F number of between 0.8 to 1.2.

* * * * *